United States Patent
Fischell et al.

(10) Patent No.: US 6,375,660 B1
(45) Date of Patent: Apr. 23, 2002

(54) STENT DELIVERY SYSTEM WITH A FIXED GUIDE WIRE

(75) Inventors: Robert E. Fischell, Dayton, MD (US); David R. Fischell, Fair Haven, NJ (US); Tim A. Fischell, Richland, MI (US)

(73) Assignee: Cordis Corporation, Warren, NJ (US)

( * ) Notice: Subject to any disclaimer, the term of this patent is extended or adjusted under 35 U.S.C. 154(b) by 0 days.

(21) Appl. No.: 09/444,104

(22) Filed: Nov. 22, 1999

(51) Int. Cl.[7] ................................. A61F 11/00
(52) U.S. Cl. ..................... 606/108; 623/1.11; 623/1.24
(58) Field of Search ..................... 606/108, 191, 606/192, 193, 194, 195, 198, 113; 604/103.04, 103.05, 103.08, 265; 623/1.11, 1.24

(56) References Cited

U.S. PATENT DOCUMENTS

| | | | | |
|---|---|---|---|---|
| 5,603,721 A | * | 2/1997 | Lau et al. ................... 606/195 |
| 5,746,745 A | * | 5/1998 | Abele et al. ................. 606/108 |
| 5,766,203 A | * | 6/1998 | Imran et al. ................. 606/198 |
| 5,792,144 A | * | 8/1998 | Fischell et al. ............. 606/108 |
| 5,840,081 A | * | 11/1998 | Andersen et al. ........... 606/108 |
| 5,891,154 A | * | 4/1999 | Loeffler ...................... 606/108 |
| 5,902,266 A | * | 5/1999 | Leone et al. ................ 606/108 |
| 6,071,285 A | * | 6/2000 | Lashinski et al. ........... 606/108 |

* cited by examiner

Primary Examiner—Pedro Philogene

(57) ABSTRACT

The present invention is a stent delivery system that uses a short section of a guide wire that is fixedly attached to a distal section of a balloon angioplasty catheter. By not having a guide wire that slides through the balloon of the balloon angioplasty catheter, the balloon on which the stent is mounted can have a reduced diameter. Therefore, the outside diameter of the undeployed stent mounted onto that balloon is also minimized. This provides a minimum profile, i.e., a minimum outside diameter, for the stent. A minimum profile at the distal section of the stent delivery system is highly advantageous for improving the percentage of cases that can be treated by direct stenting; i.e., without requiring pre-dilation of a stenosis.

21 Claims, 2 Drawing Sheets

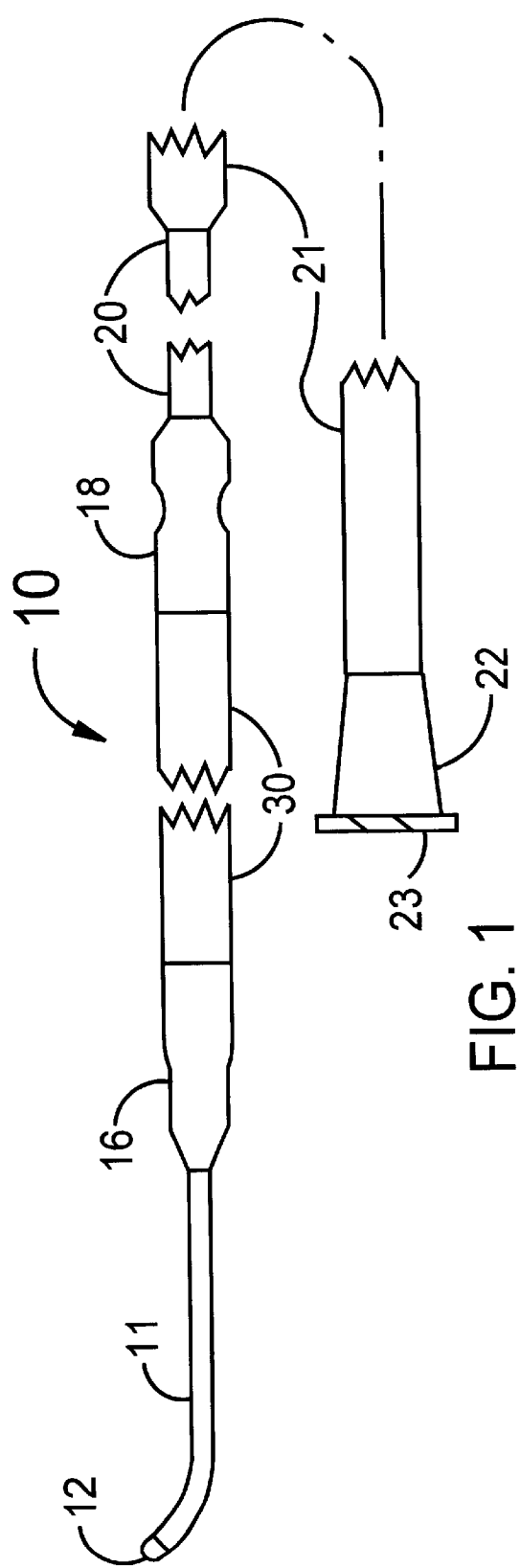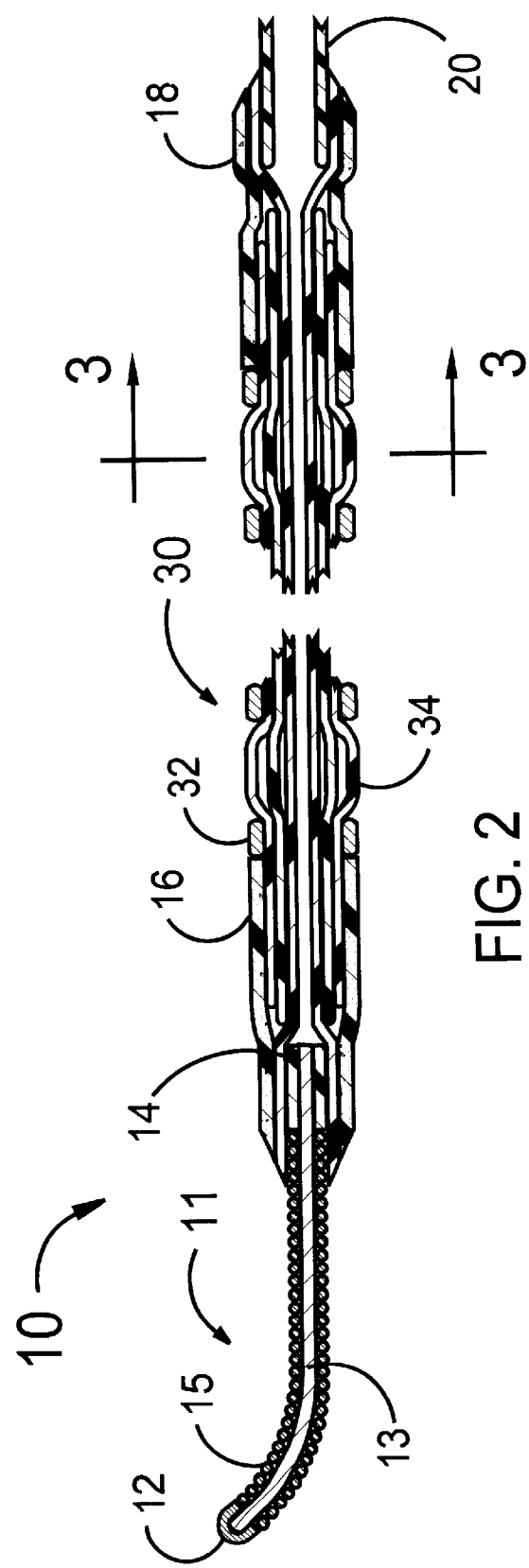

STENT DELIVERY SYSTEM WITH A FIXED GUIDE WIRE

FIELD OF USE

This invention is in the field of devices for percutaneous insertion into a vessel of the human body to place a stent at the site of an obstruction in that vessel.

BACKGROUND OF THE INVENTION

Stents are well known devices for placement in vessels of the human body to obtain and maintain patency of that vessel. The greatest use for stents has been for placement within a stenosis in a coronary artery. When a stent is used for treating a coronary artery stenosis, it has always been necessary to first place a guide wire through the stenosis. The next step in the stenting procedure is typically to pre-dilate the stenosis with a balloon angioplasty catheter that is advanced over that guide wire. The balloon angioplasty catheter is then removed and a stent delivery system that includes the stent is advanced over the guide wire and the stent is then deployed at the site of the dilated stenosis.

Recent improvements in the design of stent delivery systems has made it possible to eliminate the step of pre-dilatation for the treatment of many classes of stenoses. The delivery of a stent to the site of a stenosis without pre-dilatation has been given the name "direct stenting". However, even with direct stenting, a guide wire is still required as a precursor to advancing the stent delivery system over that guide wire to place the stent at the site of a stenosis.

SUMMARY OF THE INVENTION

The present invention is a stent delivery system that uses a short section of a guide wire that is fixedly attached to a distal section of a balloon angioplasty catheter. By not having a guide wire that slides through the balloon of the balloon angioplasty catheter, the balloon on which the stent is mounted can have a reduced diameter. Therefore, the outside diameter of the undeployed stent mounted onto that balloon is also minimized. This provides a minimum profile, i.e., a minimum outside diameter, for the stent. A minimum profile at the distal section of the stent delivery system is highly advantageous for improving the percentage of cases that can be treated by means of direct stenting; i.e., without requiring pre-dilation of a stenosis. Another advantage of the present invention is that a separate guide wire is eliminated thus saving the cost of such a guide wire. Additionally, the time to perform a stent delivery procedure is reduced because a guide wire does not have to be placed prior to using the stent delivery system to place the stent at the site of a stenosis.

Thus an object of the present invention is to provide a means for placing a stent within a vessel of the human body without requiring a separate guide wire thus saving the cost of the guide wire and also saving the time required to place a separate guide wire through an obstruction such as an arterial stenosis.

Another object of the present invention is to reduce the outside diameter (i.e., the profile) of the distal section of the stent delivery system so as to optimize the capability of the stent delivery system for direct stenting.

Still another object of the present invention is to have a guide wire fixed at the end of a balloon angioplasty catheter with a stent mounted onto the catheter's inflatable balloon and further that the length of the cylindrical portion of the inflated balloon that extends beyond each end of the stent (the "balloon overhang") is less than 1.0 mm, preferably less than 0.5 mm and optimally 0 mm; the minimum balloon overhang being advantageous for reducing the probability of arterial wall dissection beyond the edges of the stent when the balloon is inflated.

These and other important objects and advantages of this invention will become apparent from the detailed description of the invention and the associated drawings provided herein.

BRIEF DESCRIPTION OF THE DRAWING

FIG. 1 is a side view of a stent delivery system having a balloon angioplasty catheter and having a fixed guide wire extending beyond the distal end of the balloon angioplasty catheter.

FIG. 2 is a longitudinal cross section of the distal section of the stent delivery system that is shown in FIG. 1.

DETAILED DESCRIPTION OF THE INVENTION

Figure 3:
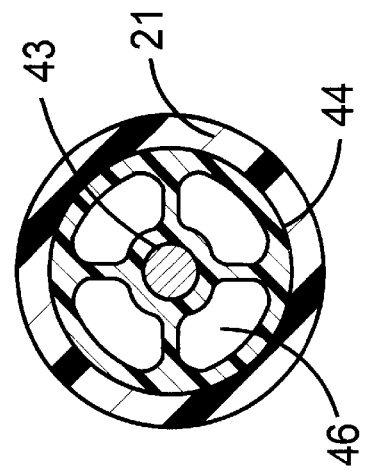
FIG. 3 is a highly enlarged transverse cross section of the distal section of the stent delivery system at section 3—3 of FIG. 2.

FIGS. 1 and 2 illustrate a stent delivery system 10 having a fixed guide wire 11 that is fixedly attached to the distal end of a balloon angioplasty catheter that has a minimum profile for the distal section of the balloon angioplasty catheter. The distal section of the stent delivery system 10 includes a guide wire 11, a proximal elastic band 18, a stent-on-balloon section 30 and a distal elastic band 16. The stent-on-balloon section 30 includes an inflatable balloon 34 onto which a balloon expandable stent 32 is co-axially mounted. A cylindrically shaped distal section of the balloon 34 is fixedly attached to a proximal section of the guide wire 11 that includes a plastic cylinder 14 that is fixedly attached to a central core wire 13 of the guide wire 11. A helical wire coil 15 is wrapped around the core wire 13 for most of the length of the core wire 13. The outside diameter of the guide wire 11 would typically be 0.014 inches. However, outside diameters between 0.008 and 0.035 inches could be used. The diameter of the core wire 13 would typically be between 0.002 and 0.014 inches. However, it should be understood that the core wire 13 could have a tapered section and could also have a flattened section situated within the wire coil 15. The flattened section of the core wire 13 is ideally suited for retaining a bend that is created by the doctor just before placing the stent delivery system 10 into a vessel of a human subject.

The material of the guide wire 11 would typically be stainless steel, tantalum, Nitnol or a combination of such metals. A distal section of the guide wire 11 could be substantially straight or it could be substantially curved as generally indicated in FIGS. 1 and 2. The curve could be as supplied by the manufacturer or it could be made or adjusted by the person placing the stent delivery system 10 into the patient. The length of the guide wire 11 that lies distal to the distal end of the balloon 34 should be approximately 1.0 to 2.0 cm and certainly less than 5 cm. Furthermore, a plastic layer with a lubricious outer surface could be substituted for the helical wire coil 15. It is also envisioned that the coil 15 could be coated with Teflon or another lubricious material.

A proximal section of the balloon 34 is fixedly attached to a distal section of a central cylindrical tube 20. The central cylindrical tube 20 would typically be formed from a plastic material such as polyurethane, polyethylene, Nylon, Teflon, or any similar plastic that is used for balloon angioplasty catheters. The outside diameter of the tube 20 would typically be between 0.5 and 2.0 mm. The length of the tube 20 would typically be between 10 and 40 cm.

The central tube 20 can be joined at its proximal end to the distal end of a proximal cylindrical tube 21. It is envisioned that the proximal tube 21 would extend for most of the length of the stent delivery system 10. A Luer fitting 22 located at the proximal end of the proximal tube 21 would be used for fluid connection by means of the attachment thread 23 to a stop-cock (not shown) to which a syringe can be attached that provides a source of inflation fluid for the balloon 34. The syringe can be used to inflate the balloon 34 with contrast medium to deploy the stent 32 into a stenosis. The syringe would also be used to deflate the balloon 34 after the stent 32 has been deployed.

FIG. 2 shows three layers of the balloon 34, which layers would typically be formed by rolling the balloon 34 in a spiral manner like a jelly-role as seen in FIG. 3. For the sake of clarity, only three layers are shown in FIG. 2 on each side of the balloon 34. To be technically correct, a total of six layers should be shown in FIG. 2 on each side of the balloon 34. Although FIG. 3 shows a rolled balloon 34, it should be understood that a conventional balloon made with a multiplicity of folded wings could also be used.

It should be understood that a conventional guide wire must be able to be torqued in order to place it into a specific artery that has the stenosis that is to treated. To be effective as a stent delivery system for direct stenting, the stent delivery system 10 must have the capability to apply torque to the guide wire 11 so that the guide wire's distal tip 12 can be selectively advanced at an arterial bifurcation into the branch artery that is to be stented.

When the stent delivery system is percutaneously placed into a vessel of a human body, the Luer fitting 22 remains exterior to that body where it can be held and rotated by the physician in order to apply a torque to rotate the distal end 12 of the guide wire 11. When a twist is applied to the Luer fitting 22, the spiral-shaped balloon 34 would tend to form a tightened spiral or would loosen depending upon the direction of the twist that is applied. By having the proximal elastic band 18 and distal elastic band 16 shrunk onto the portions of the balloon 34 that have the shape of a frustum of a cone when the balloon 34 is inflated, loosening of the spiral shape of the folded balloon 34 is prevented even if the direction of twist applied to the Luer fitting 22 would otherwise have unwound that spiral. In this manner, the structure shown in FIGS. 1 and 2 is capable of using the Luer fitting 22 to apply the torque that is required for positioning the guide wire 11 into virtually any arterial stenosis that is selected for direct stenting. It should be noted that the elastic bands 16 and 18 should be made from an elastomer such as silicone rubber. The portion of the band that lies over the balloon 34 can expand radially when the balloon 34 is inflated to deploy the stent 32. The elastic bands 16 and 18 could be solvent swelled and then placed in position or heat shrinking could be used for their placement. In either case, after placement they would snugly fit onto the balloon 34 as shown in FIGS. 1 and 2. Furthermore, the band 16 could be adhesively bonded to the guide wire 11 and/or the balloon 34. The band 18 can be adhesively bonded to the central tube 20.

Figure 5:
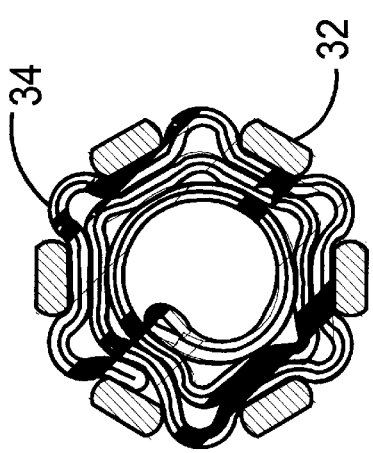
FIG. 5 is a highly enlarged transverse cross section of the stent delivery system at section 5—5 of FIG. 4 showing the connection between elongated core wire and the proximal tube of the stent delivery system.
Figure 4:
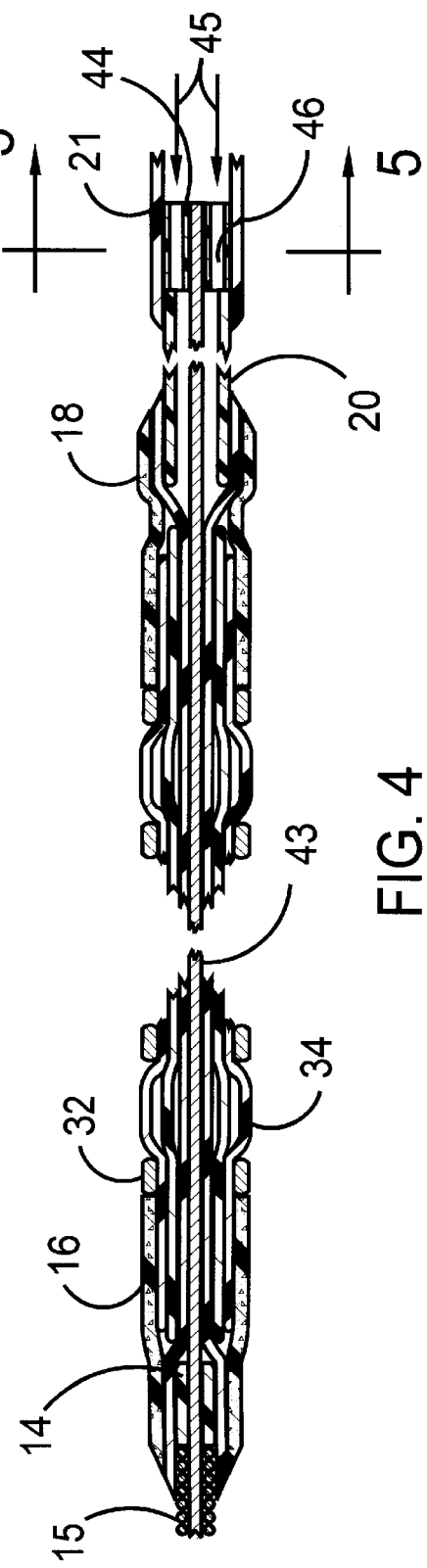
FIG. 4 is a longitudinal cross section of another embodiment of the present invention that utilizes an elongated core wire.

Another embodiment of the present invention is shown in FIGS. 4 and 5. This embodiment differs from the embodiment of FIGS. 1 and 2 in that the core wire 13 of FIGS. 1 and 2 is considerably lengthened. Explicitly, the elongated core wire 43 of FIGS. 4 and 5 extends through the balloon 34 and into and through the central tube 20. Although the elongated core wire 43 could have its proximal end terminate within the central tube 20, it would more advantageously extend into the proximal tube 21. The core wire 43 could even extend to the Luer fitting 22. The proximal end of the core wire 43 can be fixedly attached to a cylindrical, multi-lumen connector 44 that has lumens 46 through which fluid can be passed to inflate and deflate the balloon 34. The arrows 45 indicate the direction of fluid flow for inflating the balloon 34. The purpose of the elongated core wire 43 is to provide additional pushability and also to enhance the transmission of torque to the guide wire 11. Another purpose of the core wire 43 is to prevent inadvertent separation of the guide wire 11 from the stent delivery system 10. That is, it is desirable to have an additional level of safety to prevent the guide wire 11 from breaking off and embolizing downstream into the arterial circulation.

An important feature of the stent delivery system 10 would be to minimize the length of the cylindrical portion of the balloon 34 that extends beyond each end of the stent 32 when the balloon is inflated. This length is called "balloon overhang". Because the guide wire 11 cannot remain in the treated stenosis after the stent delivery system 10 is taken out of the patient, it is urgently important that edge dissections of the arterial wall that occur more frequently with longer lengths of balloon overhang be avoided. To accomplish a reduced occurrence of stent edge dissections, balloon overhang of the balloon 34 at each end of the stent 32 should be less than 1.0 mm and preferably less than 0.5 mm. Ideally, the balloon overhang should be 0±0.5 mm. How to achieve reduced balloon overhang is explained in detail in the U.S. patent application. Ser. No. 09/373,552, entitled "Stent Delivery Catheter with Enhanced Balloon Shape" which is included herein by reference.

In FIGS. 2, 3 and 4, the balloon 34 is shown to bulge outward between the struts of the stent 32. This method for holding the stent 32 more securely onto the balloon 34 is called "nesting". It is understood that the stent 32 could either be mechanically crimped onto the balloon 34 or it could be nested as described in the U.S. patent application entitled "Stent Delivery System Having a Stent Nested Onto a Non-Adhering Lubriciously Coated Balloon" that is filed on even date herewith by the same co-inventors and is included herein by reference.

It should be understood that the proximal tube 21 could extend from the proximal end of the balloon 34 to the Luer fitting 22 that is situated at the proximal end of the stent delivery system 10. That is, this invention will function satisfactorily without having a central tube 20. Furthermore, wire reinforcing in the wall of either or both the tube 20 or the tube 21 is envisioned for improving the pushability of the stent delivery system 10.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A stent delivery system for placing a stent in a vessel of the human body, the stent delivery system comprising:
   a balloon angioplasty catheter having a distal section with a single inflatable balloon located at the distal section;
   a balloon expandable stent co-axially mounted onto the inflatable balloon, the stent being adapted for permanent implantation into the vessel of the human body; and
   a flexible guide wire fixedly attached to and extending distally in a bare manner from the distal section of the balloon angioplasty catheter.

2. The stent delivery system of claim 1 wherein the guide wire is substantially straight over its entire length.

3. The stent delivery system of claim 1 wherein the guide wire has a distal section that is substantially curved.

4. The stent delivery system of claim 1 wherein the guide wire has an outside diameter that is less than 0.035 inches.

5. The stent delivery system of claim 4 wherein the guide wire has an outside diameter of 0.014 inches.

6. The stent delivery system of claim 1 wherein the length of the guide wire extending in a bare manner beyond the distal section of the balloon catheter is less than 5 cm.

7. The stent delivery system of claim 1 wherein the stent is mechanically crimped onto the balloon.

8. The stent delivery system of claim 1 wherein the stent is nested onto the balloon.

9. The stent delivery system of claim 1 wherein the balloon has a longitudinal axis and the balloon is wrapped in a spiral around the balloon's longitudinal axis prior to placement of the stent onto the balloon.

10. The stent delivery system of claim 1 wherein the balloon is folded with a multiplicity of wings as is conventional for a balloon of a balloon angioplasty catheter.

11. The stent delivery system of claim 1 wherein the balloon has a proximal section that has the shape of a frustum of a cone when the balloon is fully inflated and the balloon angioplasty catheter includes a proximal elastic band that is wrapped around the proximal section of the balloon prior to balloon inflation.

12. The stent delivery system of claim 1 wherein the balloon has a distal section that has the shape of a frustum of a cone when the balloon is fully inflated and the balloon angioplasty catheter includes a distal elastic band that is wrapped around the distal section of the balloon prior to balloon inflation.

13. The stent delivery system of claim 1 wherein the balloon has a proximal end that is fixedly attached to a central tube having a central lumen through which balloon inflation fluid can be injected or removed to respectively inflate or deflate the balloon.

14. The stent delivery system of claim 13 wherein the central tube is attached to a proximal tube that has a proximal end and a distal end, the proximal tube extending for most of the length of the stent delivery system, the proximal tube having a Luer fitting at its proximal end, the Luer fitting being adapted for connection to a source of balloon inflation fluid.

15. The stent delivery system of claim 14 wherein the flexible guide wire has a central core wire, the length of the core wire being substantially equal to the length of the guide wire.

16. The stent delivery system of claim 14 wherein the flexible guide wire has a central core wire that extends longitudinally throughout the entire length of the balloon.

17. The stent delivery system of claim 16 wherein the proximal end of the core wire is fixedly attached near the distal end of the proximal tube.

18. The stent delivery system of claim 16 wherein the proximal end of the core wire is attached near the proximal end of the proximal tube.

19. The stent delivery system of claim 1 wherein the balloon overhang length beyond each edge of the stent is less than 1.0 mm.

20. The stent delivery system of claim 1 wherein the balloon overhang length beyond each edge of the stent is less than 0.5 mm.

21. The stent delivery system of claim 1 wherein the longitudinal length of the stent when deployed is approximately equal to the length of the cylindrical section of the inflated balloon thereby resulting in an approximately zero length of balloon overhang beyond the edges of the stent.

* * * * *